United States Patent
Beech, Jr. et al.

(10) Patent No.: US 7,790,941 B2
(45) Date of Patent: Sep. 7, 2010

(54) OXYGENATE-TO-OLEFIN CONVERSIONS IN A BAFFLED REACTOR

(75) Inventors: James H. Beech, Jr., Kingswood, TX (US); Nicolas Coute, Houston, TX (US); Jeffrey S. Smith, Texas City, TX (US); Michael Peter Nicoletti, Houston, TX (US); Charles O. Bolthrunis, Nahant, MA (US); Domenic C. Ferrari, Lexington, MA (US); Umesh K. Jayaswal, Lexington, MA (US); Roy Walter Silverman, Winchester, MA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 885 days.

(21) Appl. No.: 11/435,110

(22) Filed: May 16, 2006

(65) Prior Publication Data

US 2006/0270884 A1    Nov. 30, 2006

Related U.S. Application Data

(60) Provisional application No. 60/685,346, filed on May 27, 2005.

(51) Int. Cl.
*C07C 1/00* (2006.01)
*B01J 19/00* (2006.01)
*B01J 8/18* (2006.01)

(52) U.S. Cl. ........ 585/639; 585/327; 585/328; 585/329; 585/638; 585/640; 422/49; 422/131; 422/139; 422/145; 422/149

(58) Field of Classification Search .......... 585/327, 585/328, 329, 638, 639, 640; 422/49, 131, 422/139, 145, 149
See application file for complete search history.

(56) References Cited

U.S. PATENT DOCUMENTS

| | | | |
|---|---|---|---|
| 4,138,440 A | 2/1979 | Chang et al. | |
| 4,238,631 A | 12/1980 | Daviduk et al. | |
| 4,251,484 A | 2/1981 | Daviduk et al. | |
| 6,166,282 A | 12/2000 | Miller | |
| 6,455,747 B1 * | 9/2002 | Lattner et al. | 585/638 |
| 2003/0194356 A1 * | 10/2003 | Meier et al. | 422/141 |
| 2004/0024276 A1 | 2/2004 | Smith et al. | |

FOREIGN PATENT DOCUMENTS

EP           099 690        1/1984

OTHER PUBLICATIONS

F.J. Keil, "Methanol-to-hydrocarbons: process technology", Microporous and Mesoporous Materials, vol. 29, pp. 49-66, 1999.

* cited by examiner

*Primary Examiner*—Glenn Caldarola
*Assistant Examiner*—Prem C. Singh
(74) *Attorney, Agent, or Firm*—Kevin M. Faulkner; David M. Weisberg; Frank E. Reid

(57) ABSTRACT

The invention concerns methods and systems for minimizing back-mixing of feedstock flow in converting oxygenates to olefins. In one embodiment, back-mixing is reduced by providing a reactor that includes baffles to reduce the hydraulic diameter of at least a portion of the reactor. Some or all of the baffles can also serve as cooling tubes for reducing temperature gradients in the reactor, and thereby maximize light olefin production.

19 Claims, 7 Drawing Sheets

OXYGENATE-TO-OLEFIN CONVERSIONS IN A BAFFLED REACTOR

CROSS-REFERENCE TO RELATED APPLICATIONS

This application claims benefit of Provisional Application No. 60/685,346, filed May 27, 2005, the disclosure of which is fully incorporated herein by reference.

FIELD OF THE INVENTION

The invention relates to methods and systems for converting oxygenates to olefins. In particular, the invention relates to methods and systems for minimizing back-mixing of feedstock flow in converting oxygenates to olefins.

BACKGROUND OF THE INVENTION

In industrial scale reactions for hydrocarbon to olefin conversion, the desired products are typically lighter olefins such as ethylene and propylene. During these industrial processes, it is desirable to achieve nearly complete conversion of the oxygenate feedstock to olefins, such as the light olefins ethylene and propylene. In addition to controlling the overall conversion rate and the light olefin selectivity, it can also be desirable to control the ratio of ethylene to propylene produced by a reaction. A further consideration in conversion reactions is the cost required to perform the conversion reaction. A conventional reactor for performing a controlled oxygenates-to-olefin reaction can require multiple risers of nearly 200 feet in height and hundreds of tons of catalyst for converting the oxygenate feedstock.

U.S. Pat. No. 6,166,282 B1 discloses a process for converting oxygenates to olefins in a reactor with two reaction zones. Feedstock is introduced into a lower, dense phase zone from a single inlet to effect a partial conversion to light olefins. The dense phase zone includes a fluidized catalyst bed. It is disclosed that as the feedstock continues to move up in the reactor, it moves into a transition zone above the dense phase zone where the reaction continues essentially to completion. The dense phase zone operates at a superficial velocity of less than 1 meter per second, and the transition zone operates at a superficial velocity of from 1 to 4 meters per second.

United States Patent Application Publication No. 2004/0024276 describes a process for converting oxygenates to olefins in a reactor with a lower reaction zone and an upper reaction zone. Feedstock is introduced into the lower reaction zone, which includes a fluidized catalyst bed. It is disclosed that as the feedstock continues to move up in the reactor, the feedstock moves into the upper reaction zone having a smaller average diameter than the lower reaction zone. The upper reaction zone has a ratio of height versus average diameter of at least 5 to 1 but not greater than 100 to 1. The feedstock is further reacted in this second reaction zone. The lower reaction zone operates at a superficial velocity of at least 0.5 meters per second and up to about 10 meters per second, while the second reaction zone operates at a superficial velocity of at least 1 meter per second and up to about 25 meters per second.

U.S. Pat. No. 4,251,484 discloses a process for converting methanol and other lower alcohols and ethers to gasoline-type hydrocarbons. Baffle tubes, possibly including heat exchanger tubes, are placed in the reactor within a region having a fluidized bed of a zeolite catalyst. The disclosed range of catalyst bed densities is between 27 lbs/ft$^3$ (432.5 kg/m$^3$) and 35 lbs/ft$^3$ (560.6 kg/m$^3$), with a nominal gas velocity of about 2 ft/sec (0.61 m/sec) for the methanol passing through the catalyst bed. During a conversion reaction, the temperature of the catalyst bed is no greater than 775° F. After conversion, catalyst is separated from the product gas flow using conventional cyclone separators.

What is needed is a system and method for converting oxygenates to olefins that provides improved control over the process conditions. The process should allow for control over the ratio of ethylene and propylene produced. The process should also be able to be performed in a reactor having reduced dimensions and/or a lower catalyst requirement in the reactor.

SUMMARY OF THE INVENTION

This invention provides a system and method for performing an oxygenates-to-olefin reaction so that back-mixing of the feedstock flow is minimized and a practical reactor size is maintained. This allows for improved production of desirable light olefins (i.e., ethylene and propylene) while maintaining a desirable level of feedstock throughput in the reactor.

According to one aspect of the invention, there is provided a method for converting oxygenates to olefins. The method comprises contacting a catalyst, preferably a metalloaluminophosphate catalyst, more preferably a silicoaluminophosphate molecular sieve, with an oxygenate feedstock in an initial conduit. The catalyst and oxygenate feedstock are flowed through a contacting conduit containing a plurality of baffles and having a diameter larger than the initial conduit at a superficial velocity of 6 feet per second (1.83 m/sec) or greater. The catalyst is passed into a connecting conduit having a diameter smaller than the contacting conduit. In one embodiment, an axial Peclet number for a gas portion of the flow is 8 or more so that back-mixing is reduced. In another embodiment, the contacting conduit has a hydraulic diameter of 72 inches (1.83 m) or less.

In one embodiment of the invention, the connecting conduit further comprises at least one baffle to further reduce back-mixing. In yet another embodiment of the invention, the connecting conduit has a Peclet number greater than the Peclet number of the contacting conduit. Preferably, a temperature gradient from an entrance of the contacting conduit to an exit of the contacting conduit is 100° C. or less, more preferably 50° C. or less, and most preferably, 20° C. or less.

In another embodiment, one or more of the baffles in the contacting conduit comprise a cooling tube. In a particular embodiment, the temperature gradient is maintained by flowing at least one of steam and boiling water through the one or more cooling tubes. In another embodiment, the temperature gradient is maintained by flowing boiling water through a first plurality of cooling tubes and flowing steam through a second plurality of cooling tubes.

In yet another embodiment, the catalyst and feedstock flow leave the contacting conduit at a temperature of 400° C. or greater. In another embodiment, at least a portion of the contacting conduit has a hydraulic diameter of from about 8 inches (0.2 m) to about 24 inches (0.61 m).

The catalyst and feedstock flowing through the contacting conduit preferably flow at a catalyst density of from 4 lb/ft$^3$ (64.07 kg/m$^3$) to 20 lb/ft$^3$ (320.4 kg/m$^3$). More preferably, the catalyst and feedstock flowing through the contacting conduit flow at a catalyst density of from 8 lb/ft$^3$ (128.1 kg/m$^3$) to 12 lb/ft$^3$ (192.2 kg/m$^3$).

In another embodiment, the catalyst and feedstock flowing through the contacting conduit flow at a superficial gas velocity of from 0.5 ft/sec (1.52 m/sec) to 20 ft/sec (6.1 m/sec). Preferably, the catalyst and feedstock flowing through the contacting conduit flow at a superficial gas velocity of from 8 ft/sec (2.44 m/sec) to 15 ft/sec (4.57 m/sec).

In one embodiment of the invention, the temperature gradient is maintained by selecting a temperature for the exit of the contacting conduit; and controlling a temperature at the entrance of the contacting conduit to achieve a desired ratio of $C_2$ olefins versus $C_3$ olefins. Preferably, the ratio of $C_2$ olefins to $C_3$ olefins ranges from about 0.8 to 1 to about 1.2 to 1.

According to another aspect of the invention, there is provided a system for converting oxygenates to olefins. The system, or apparatus includes an initial conduit having at least one feedstock input and at least one catalyst input. A contacting conduit containing a plurality of baffles is openly joined to the initial conduit, and at least a portion of the contacting conduit has a hydraulic diameter of 72 inches (1.83 m) or less. A connecting conduit is openly joined to the contacting conduit. A plurality of primary separation devices is in fluid communication with the connecting conduit, and comprise cyclone separators having a height to diameter ratio of 5 or less. A plurality of secondary separation devices is in fluid communication with the primary separation devices, and a plurality of tertiary separation devices is joined to the secondary separation devices by a plenum.

Any two or more of the above embodiments or aspects of the invention that are not in conflict with one another can be combined to form additional embodiments of the invention that are not specifically described above.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

Figure 1:
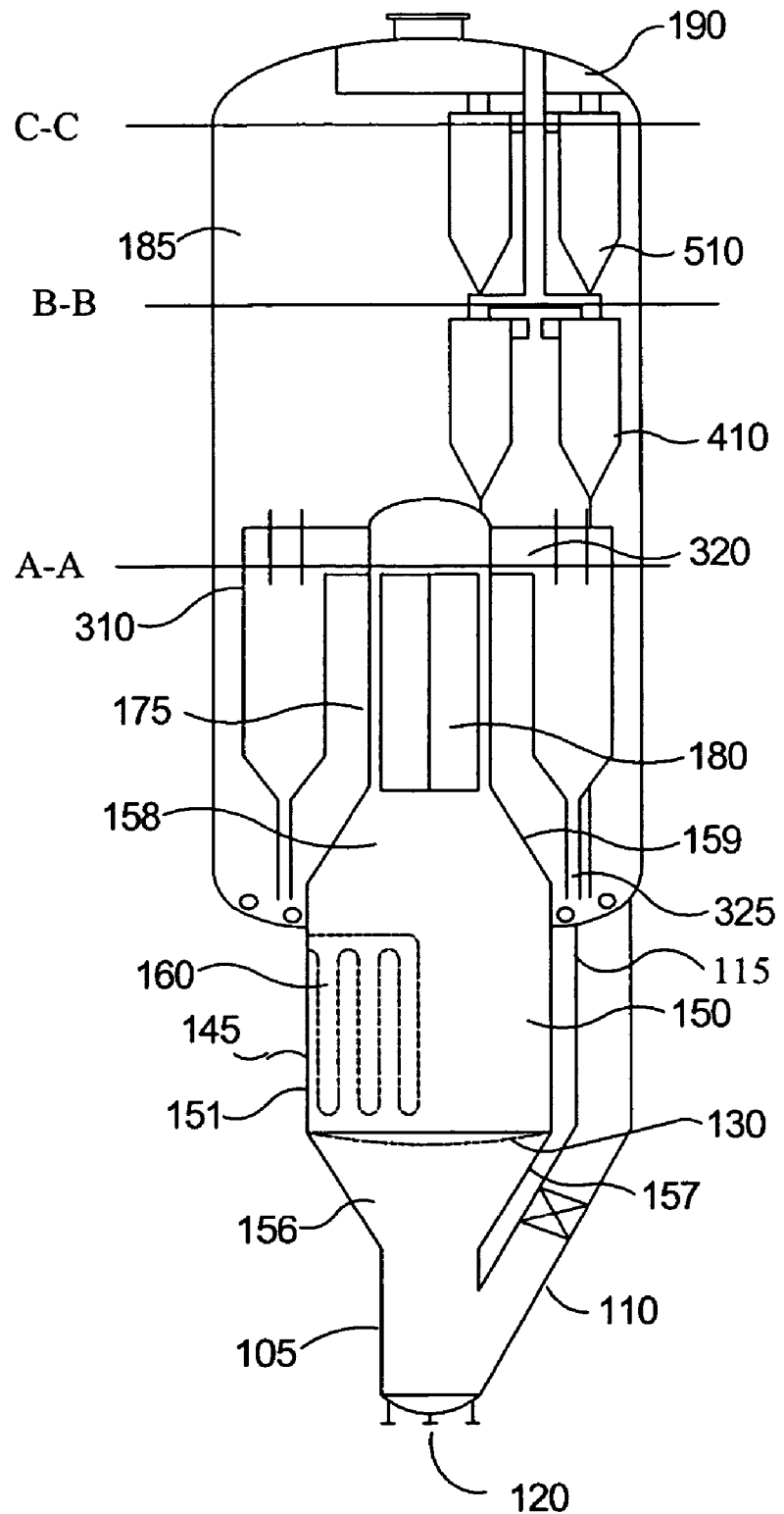
FIG. 1 illustrates a reactor according to an embodiment of the invention.

I. Overview of Reduced Size Reactor with Minimal Back-Mixing

This invention provides a system and method for performing an oxygenates-to-olefin reaction. The system and method minimize back-mixing of the feedstock flow while maintaining a practical reactor size. This allows for improved production of desirable light olefins while maintaining a desirable level of feedstock throughput in the reactor. The system and method also allow for reduction or minimization of temperature gradients in the reactor, which provides further control over the relative amounts of ethylene and propylene produced during a conversion reaction.

In an embodiment, the above advantages are achieved in part by providing a reactor having one or more baffled reaction zones. A baffled reaction zone allows a reactor with a larger diameter to behave like a plurality of reactors that each have a smaller effective diameter. A feedstock flow is introduced into the reactor and contacted with catalyst as the flow passes through the reaction zones of the reactor. The feedstock is flowed through the reactor at a velocity sufficient to minimize back-mixing of the feedstock flow. However, the smaller effective diameter (or hydraulic diameter) of the one or more baffled reaction zones allows back-mixing to be minimized at a lower feedstock velocity as compared to a reactor of the same size that does not include baffles. Alternatively, the baffled reaction zone allows a minimum desired Peclet number for the flow to be achieved at a lower velocity. By avoiding back-mixing at a reduced superficial velocity, the feedstock can be reacted in a controlled manner in a smaller reactor volume. In another embodiment, the reactor can include at least two separate baffled reaction zones.

In still another embodiment, the above advantages can be achieved in part by having some or all of the baffles in the baffled reaction zone serve as cooling tubes. During a conversion reaction, the cooling tubes are used to reduce or minimize a temperature gradient across a given reaction zone. Reducing the temperature gradient has a small impact on the overall olefin yield. Desirably, reducing the temperature gradient improves the ratio of ethylene produced as compared to propylene.

II. Reactor Configuration

A. Reactor Structure—in General

In an embodiment, a flow of oxygenate feedstock is fed into a reactor, such as into an initial conduit in the reactor. The oxygenate feedstock can enter the reactor through one or more feed nozzles. The one or more feed nozzles enter the reactor through the bottom of the reactor. A fluidized flow of catalyst is also introduced into the lower portion of the reactor, such as an initial conduit in the reactor. The catalyst entering the reactor can be fresh catalyst or the catalyst can be recirculated from separation devices. In an embodiment, the catalyst is stripped of excess hydrocarbons and/or regenerated prior to entering the lower portion of the reactor. As the feedstock and catalyst flows enter the reactor, the feedstock and catalyst will be mixed together and come into contact. The feedstock and catalyst will continue to contact each other as they flow upward in the reactor.

After the feedstock and catalyst flows enter the initial conduit in the lower reaction zone, the feedstock and catalyst flow toward a contacting conduit. In an embodiment, the contacting conduit is composed of a lower frustum, a barrel containing a plurality of baffles and/or cooling tubes, and an upper frustum. The lower frustum corresponds to an increase in the diameter of the reactor to transition from the diameter of the initial conduit to the diameter of the barrel portion of the contacting conduit. Similarly, the upper frustum corresponds to a decrease in the size of the reactor from the diameter of the barrel to the diameter of the connecting conduit.

In an embodiment, the height of the barrel is at least 15 feet (4.57 m), or at least 20 feet (6.1 m), or at least 25 feet (7.62 m), or at least 30 feet (9.14 m). In another embodiment, the height of the barrel is 50 feet (15.24 m) or less, or 45 feet (13.72 m) or less, or 40 feet (12.19 m) or less, or 35 feet (10.67 m) or less, or 30 feet (9.14 m) or less.

In an embodiment, the contacting conduit can optionally include a distributor, such as a perforated distributor located at the place where the lower frustum is openly joined to the barrel of the contacting conduit. The distributor aids in distributing the feedstock and catalyst flow over the entire width of the barrel section. In an embodiment, a distributor plate is used that is a perforated plate having substantially the same diameter as the interior of the barrel. The plate can be perforated with a plurality of regularly spaced holes, such as 2-, 3-, 4- or 5-inch (0.05, 0.08, 0.1 or 0.13 m) holes regularly arranged, such as on a 6-, 7-, 8- or 10-inch (0.15, 0.18, 0.2, or 0.25 m) square pitch.

After passing through the contacting conduit, the feedstock and catalyst flow passes into the connecting conduit. In an embodiment, the connecting conduit is openly joined to an upper frustum of the contacting conduit. In an embodiment, the connecting conduit can be a single conduit or riser, or the connecting conduit can contain a baffle structure to effectively provide 2, 3, 4, or more conduits with smaller hydraulic diameters. The connecting conduit is joined to one or more cyclones or other separation devices for separating any catalyst particles entrained in the flow from the reacted feedstock. The reacted feedstock exits from the reactor, while the separated catalyst can be returned to the initial conduit for further reaction.

FIG. 1 provides an example of a reactor suitable for performing the method of this invention. Catalyst enters the reactor through one or more catalyst inlets 110. In an embodiment, at least a portion of the catalyst entering the reactor through catalyst inlet 110 is returned from a recirculation loop that includes a regenerator. Other catalyst inlets (not shown) can be used to add additional catalyst to the reactor, such as catalyst to make up for catalyst losses during reactor operation. The catalyst from catalyst inlet 110 enters the reactor in initial conduit 105.

Feedstock inlets 120 are openly joined to the initial conduit 105 of reactor 10 at or near the bottom of the reactor. Feedstock inlets 120 can introduce feedstock vertically into the reactor 10, as shown in FIG. 1, or feedstock inlets 120 can form a non-zero angle relative to vertical as they enter the reactor.

Initial conduit 105 is openly joined to contacting conduit 145. In an embodiment, contacting conduit 145 is composed of a bottom frustum 156, a barrel 150, and an upper frustum 158. In an embodiment, sidewall 157 of bottom frustum 156 is angled so that the diameter of the frustum increases in the direction away from feedstock inlets 120.

Within contacting conduit 145, bottom frustum 156 is openly joined to barrel 150. At or near the point where bottom frustum 156 openly joins barrel 150, an optional distributor plate 130 is provided to allow for more even distribution of incoming feedstock. Barrel 150 should be tall enough to at least contain the full height of any baffles or cooling tubes 160 contained in the contacting conduit 145. Sidewall 151 of barrel 150 is a vertical sidewall. Barrel 150 is openly joined to upper frustum 158. Upper frustum 158 narrows the width of the reactor back to the final desired dimension for connecting conduit 175. In an embodiment, the angle between sidewall 159 and sidewall 151 is the same as the angle between sidewall 157 and sidewall 151.

Figure 8:
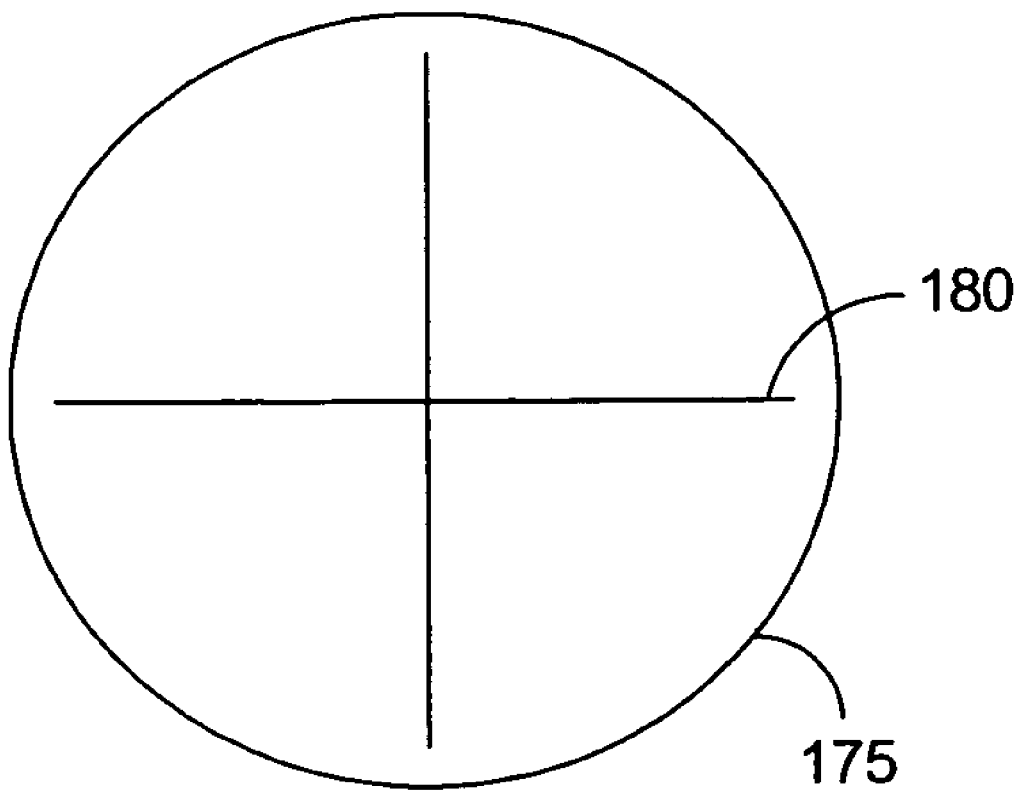
FIG. 8 illustrates a cross-sectional view of a baffled portion of a reactor according to an embodiment of the invention.

In the embodiment shown in FIG. 1, connecting conduit 175 includes an optional vertical baffle 180. FIG. 8 schematically shows a connecting conduit containing a vertical baffle according to an embodiment of the invention. In the embodiment shown in FIG. 8, vertical baffle 180 divides connecting conduit 175 into 4 regions each having an equal volume. In another embodiment, a vertical baffle can divide the connecting conduit into a plurality of regions, such as 2 regions, or 3 regions, or 5 regions, or 6 regions, or 8 regions. By dividing the connecting conduit into a plurality of regions, the hydraulic diameter of the connecting conduit can be reduced to 72 inches (1.83 m) or less, or 36 inches (0.91 m) or less, or 24 inches (0.61 m) or less, or 12 inches (0.3 m) or less, or 10 inches (0.25 m) or less, or 8 inches (0.2 m) or less. Alternatively, the baffles can reduce the hydraulic diameter of the connecting conduit by a factor of 2, or a factor of 3, or a factor of 4. In still another embodiment, the regions can have varying volumes. In yet another embodiment, the connecting conduit can include vertical baffles.

In the embodiment depicted in FIG. 1, the diameter of initial conduit 105 is 10 feet (3.05 m). The diameter of barrel 145 is 24 feet (7.32 m), while the diameter of connecting conduit 175 is 12 feet (3.66 m). The change in width between these sections, in combination with the baffles and/or cooling tubes 160, aids in the development of the desired flow regimes. Similarly, the baffles 180 present in connecting conduit 175 aid in developing a desired flow region.

B. Baffles

In an embodiment, at least a portion of the connecting conduit includes a plurality of baffles. The baffles are distributed throughout the portion of the connecting conduit in order to reduce the hydraulic diameter of the connecting conduit. The baffles can be distributed in any convenient configuration, but preferably the baffles are separated by a regular distance from each other. Preferably, the baffles are in a barrel portion of the connecting conduit.

In an embodiment, the baffles can be round, square, elliptical, rectangular, or any other convenient shape. In the following examples, baffles will be referred to in terms of one dimension (width or diameter). However, this is done for convenience, and baffles having elliptical shapes or other shapes requiring more than one lateral dimension for characterization may also be used. In an embodiment, the width or diameter of the baffles is half of the separation distance between the baffles. For example, if the separation between the baffles is 8 inches (0.2 m), the baffles are selected to have a width or diameter of at least 4-inches (0.1 m). In other embodiments, the baffles are selected to have a width or diameter of at least 1 inch (0.03 m), or at least 2 inches (0.05 m), or at least 3 inches (0.08 m), or at least 5 inches (0.13 m), or at least 6 inches (0.15 m).

In an embodiment where the contacting conduit has a larger diameter than the initial conduit or connecting conduit, the reactor can have two frustum shaped sections to allow for the expansion and contraction of the diameter of the reactor. In such an embodiment, the height of the baffles is less than the distance between the two frustums. For example, if the portion of the contacting conduit between the two frustums is 30 feet (9.14 m), the baffles can have a height of 25 feet (7.62 m) or less, or 20 feet (6.1 m) or less, or 15 feet (4.57 m) or less. Alternatively, the baffles can have a height of 10 feet (3.05 m) or more, or 15 feet (4.57 m) or more, or 20 feet (6.1 m) or more. In other embodiments, the baffles can have a height that is proportional to the height of the contacting conduit between the frustums. For example, relative to the height of the contacting conduit between the frustums, the baffles can have a height of 85% or less of the height of the contacting conduit, or 80% or less, or 70% or less, or 60% or less. Alternatively, the baffle height can be 50% or more of the height of the contacting conduit, or 60% or more, or 70% or more.

Arranging baffles within the barrel or another conduit reduces the effective hydraulic diameter of the conduit. From a fluid flow perspective, the baffles convert the single, large diameter conduit into many smaller diameter reaction areas. In an embodiment, the baffles are arranged to have a regular pitch between them. For example, the baffles can be spaced apart by a distance of 4 inches (0.1 m) or more, or 6 inches (0.15 m) or more, or 8 inches (0.2 m) or more, or 10 inches (0.25 m) or more, or 12 inches (0.3 m) or more, or 24 inches (0.61 m) or more. Alternatively, the baffles can be spaced apart by a distance of 72 inches (1.83 m) or less, or 36 inches (0.91 m) or less, or 24 inches (0.61 m) or less, or 12 inches (0.3 m) or less, or 10 inches (0.25 m) or less, or 8 inches (0.2 m) or less. In still another embodiment, the spacing between the baffles can be twice the diameter of the baffles. In an embodiment, the baffles can be arranged on a square pitch, a triangular pitch, or in any other convenient regular configuration. In another embodiment, the baffles can be spaced in an irregular manner.

Figure 2:
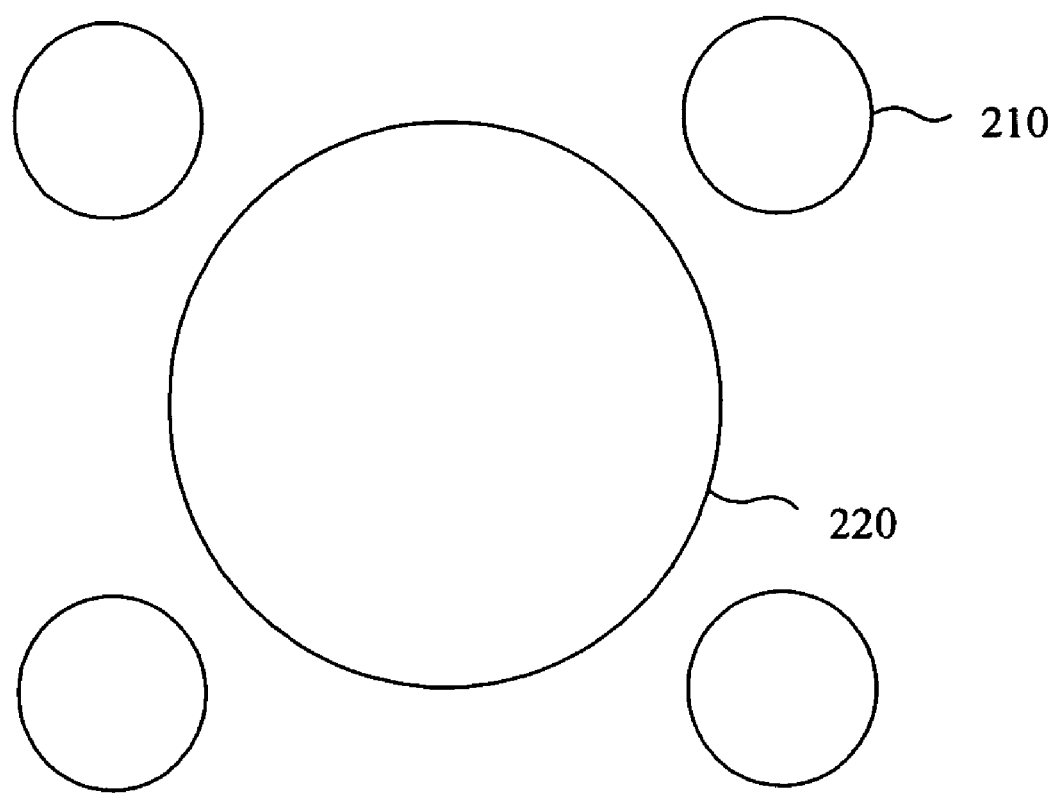
FIG. 2 illustrates a portion of a baffled reactor according to an embodiment of the invention.

FIG. 2 provides an example of how baffles reduce the hydraulic diameter of a conduit. FIG. 2 shows a top down view of a small group of baffles within a reactor according to an embodiment of the invention. In FIG. 2, each baffle 210 has a diameter of 4 inches (0.1 m) while the baffles are arranged on a square grid with grid points separated by 8 inches (0.2 m). A circle 220 is drawn between the baffles. The circle 220 roughly represents the effective hydraulic diameter of the space between the baffles. As shown in FIG. 2, this configuration produces an effective hydraulic diameter of roughly 10 inches. In another embodiment, the baffles in a conduit can be arranged to produce a hydraulic diameter of 72 inches (1.83 m) or less, or 36 inches (0.91 m) or less, or 24 inches (0.61 m) or less, or 12 inches (0.3 m) or less, or 10 inches (0.25 m) or less, or 8 inches (0.2 m) or less.

C. Cooling Tubes

In another embodiment, some or all of the baffles can be in the form of cooling tubes. The cooling tubes can have the same general shape and width/diameter as the baffles, or the shape and dimension of the cooling tubes can be selected independently. In an embodiment, the width or diameter of the cooling tubes is at least 1 inch (0.03 m), or at least 2 inches (0.05 m), or at least 3 inches (0.08 m), or at least 4 inches (0.1 m), or at least 5 inches (0.13 m), or at least 6 inches (0.15 m).

In an embodiment, the cooling tubes are in fluid communication with a source of hot or boiling water, steam, or another cooling fluid. By circulating a cooling fluid through the cooling tubes, the temperature of the reactor region containing the cooling tubes can be regulated. During an oxygenates-to-olefin reaction, the temperature inside the reactor will be higher than the temperature of the cooling fluid. Thus, heat will be transferred to the cooling tubes from the inside of the reactor. The greater the temperature difference is between the cooling tubes and the interior of the reactor, the greater the heat transfer. If the temperature varies within the portion of the reactor containing the cooling tubes, the higher temperature portions of the reactor will be cooled proportionally more than the lower temperature portions. As a result, the cooling tubes can be used to reduce temperature differences or gradients within the reactor.

Alternatively, some cooling tubes can circulate one cooling fluid, such as hot (boiling) water, while other cooling tubes circulate a second cooling fluid, such as steam. Circulating two types of cooling fluids can provide additional control over the temperature within a reactor. For example, a cooling tube circulating boiling water may be able to absorb larger amounts of heat by converting water into steam. On the other hand, a cooling tube circulating steam can provide finer control over the temperature within the reactor. Providing a mix of these types of cooling tubes can provide greater flexibility in maintaining a desired temperature profile within the reactor.

D. Catalyst Separators

After passing through the connecting conduit, the flow of reacted feedstock and catalyst (as well as any unreacted feedstock) passes into one or more separation devices. In an embodiment, the flow of feedstock and catalyst particles passes into a plurality of multi-stage cyclone separators, such as a plurality of three-stage cyclone separator. In such an embodiment, each cyclone stage can be a conventional cyclone separator.

In another embodiment, the first separator stage of some or all of the multi-stage separators can be another type of separation device, such as a "rough cut" cyclone. One way to characterize a cyclone is by using a ratio of the height of the cyclone from the top of the cyclone to the vortex of the cone leading to the dipleg versus the diameter of the barrel of the cyclone. The height to diameter ratio for a conventional cyclone with greater than 99% efficiency is typically 5 or greater. However, a "rough cut" cyclone with an efficiency near 99% can still be created with a smaller height to diameter ratio. In an embodiment, the first separator stage can be a rough cut cyclone having a height to diameter ratio of 4.5 or less, or 4.0 or less, or 3.5 or less.

Each of the first separator stages separates an incoming flow of feedstock and catalyst particles into a higher density flow and a lower density flow. The higher density flow is composed primarily of catalyst particles. The higher density flow from each first separator stage is eventually returned to the bed of catalyst particles in the reactor. However, some or all of the catalyst particles in this higher density flow can be further processed before rejoining the catalyst bed. In an embodiment, at least a portion of the catalyst particles can be exposed to a flow of steam or some other gas suitable for stripping any remaining hydrocarbons out of the catalyst particles. In another embodiment, at least a portion of the catalyst particles can be passed through a regenerator to remove coke that has accumulated on the surface of the particles.

The lower density flow exits through the top of each first separator stage and passes on to any additional separator stages in the separation device, such as second and third cyclone stages. The additional separator stages also produce a higher and lower density output. For each of the additional separator stages, the higher density output corresponds to catalyst that is returned to the initial conduit for further reaction, while the lower density output corresponds to the reacted feedstock product that contains less catalyst due to the separation. In an embodiment, the lower density output of the second separator stage is joined to the input of the third separator stage, while the lower density output of the third separator stage exits the reactor.

In an embodiment, the lower density output of each second separator stage can be joined to the input of each corresponding third separator stage in a conventional manner. In another preferred embodiment, the lower density output of some or all of the second separator stages is openly joined to the input of some or all of the third separator stages using an annular plenum. The annular plenum collects the lower density output from each of second separator stages. The plenum includes a hole in the top of the plenum corresponding to each third stage separator. During operation, the lower density outputs from each second separator stage are directed into the plenum. The flow in the plenum then passes into the third stage separators via the holes in the top of the plenum. In an embodiment, the plenum is an interior plenum, with the second and third separator stages located around the plenum.

FIG. 1 depicts a reactor that uses a plurality of multi-stage cyclone separators for separating catalyst from the reacted feedstock flow. For clarity, only a representative sample of the total number of cyclones are depicted. In FIG. 1, a reacted feedstock flow exiting connecting conduit 175 is directed into an inlet 320 of a rough cut cyclones 310. The higher density output from the rough cut cyclones 310 passes out through a dipleg 325 for eventual return to initial conduit 105 via return conduit 115 and catalyst inlet 110. The lower density output of the the rough cut cyclones 310 exits into disengaging shell 185 and passes into the secondary cyclones 410. The lower density output from the secondary cyclones 410 is directed into a plenum for entry into one or more tertiary cyclones 510. The output from tertiary cyclones 510 is directed into an exit plenum 190. The reactor shown in FIG. 1 has 8 rough cut cyclones, 24 secondary cyclones, and 24 tertiary cyclones.

Figure 3:
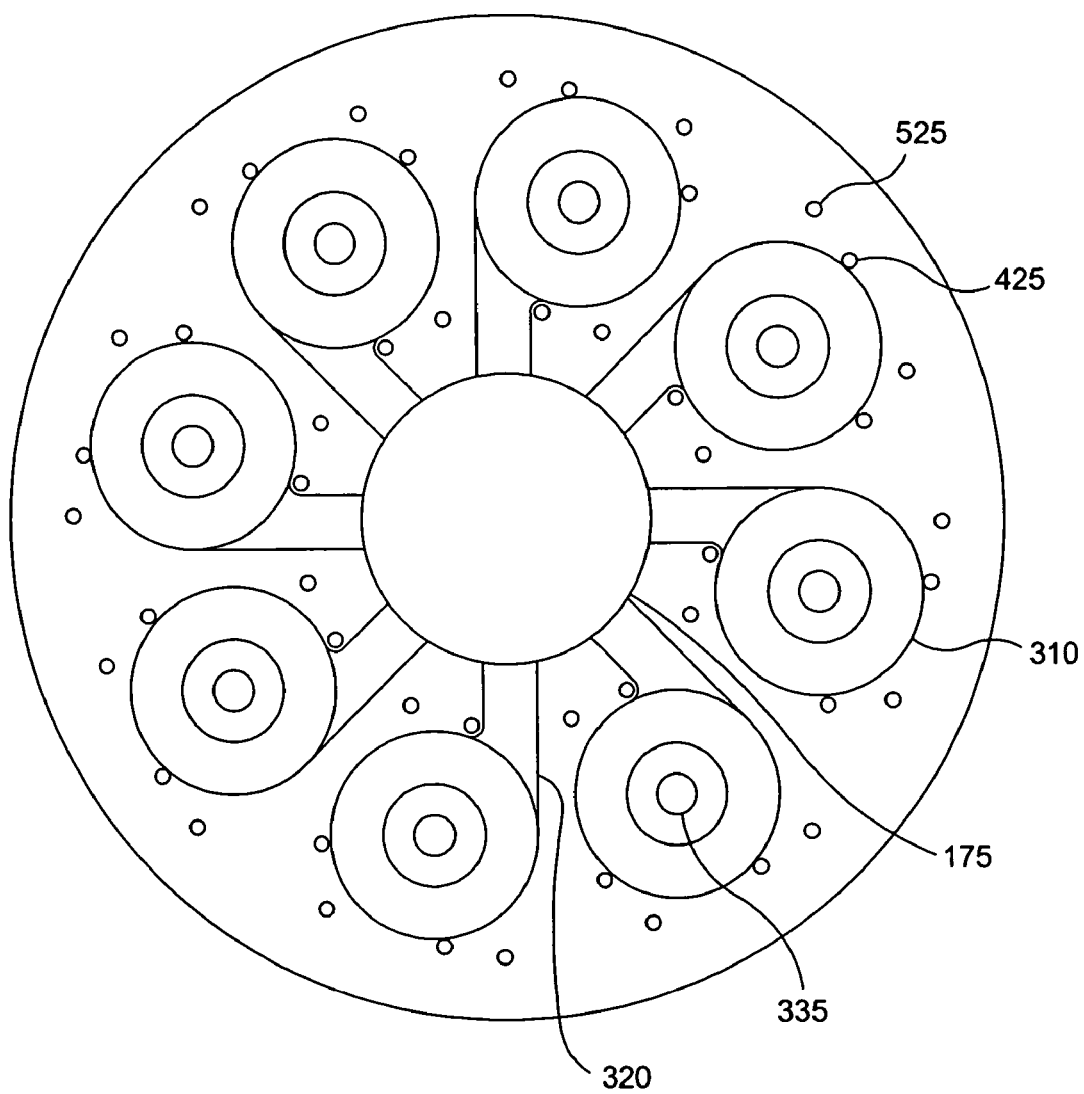
FIG. 3 illustrates a sectional view of the reactor of FIG. 1.

FIG. 3 shows a top down view of the rough cut cyclones taken along section line "A-A" as shown in FIG. 1. Each of the rough cut cyclones 310 is connected to connecting conduit 175 by an inlet 320. FIG. 3 also shows the locations of diplegs 425 of the secondary cyclones and diplegs 525 for the tertiary cyclones. The lower density output of each rough cut cyclone exits the cyclone through output 335 into the separation shell.

Figure 4:
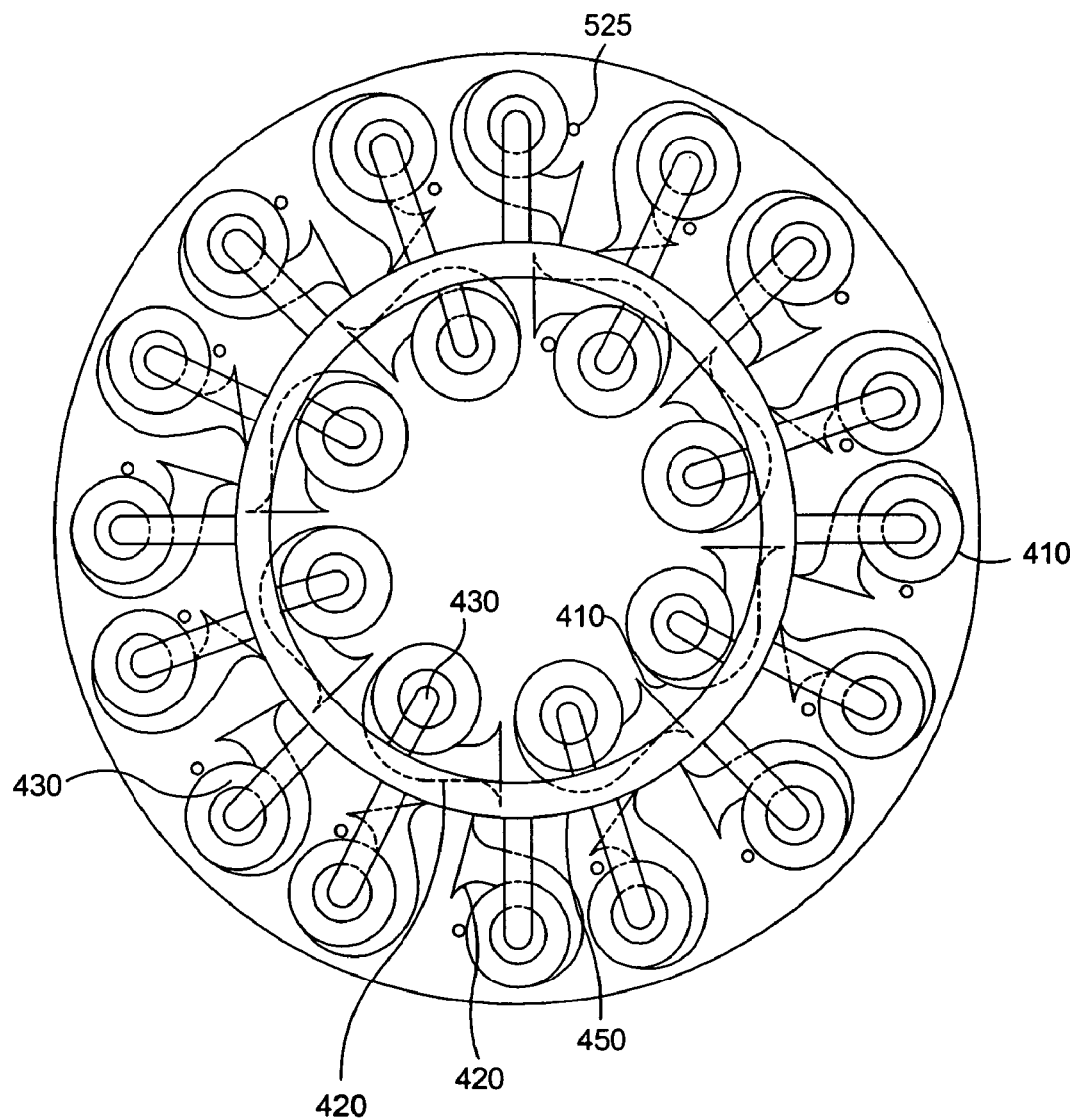
FIG. 4 illustrates another sectional view of the reactor of FIG. 1.

FIG. 4 shows a top down view of the secondary cyclones 410 along a section line "B-B" as shown in FIG. 1. Secondary cyclone inlets 420 take in the output from the rough cut cyclones for further separation of catalyst from the product flow. The lower density output from secondary cyclones 410 passes through secondary outlets 430 into an interior plenum 450. The location of the diplegs 525 for the tertiary cyclones is also shown.

Figure 5:
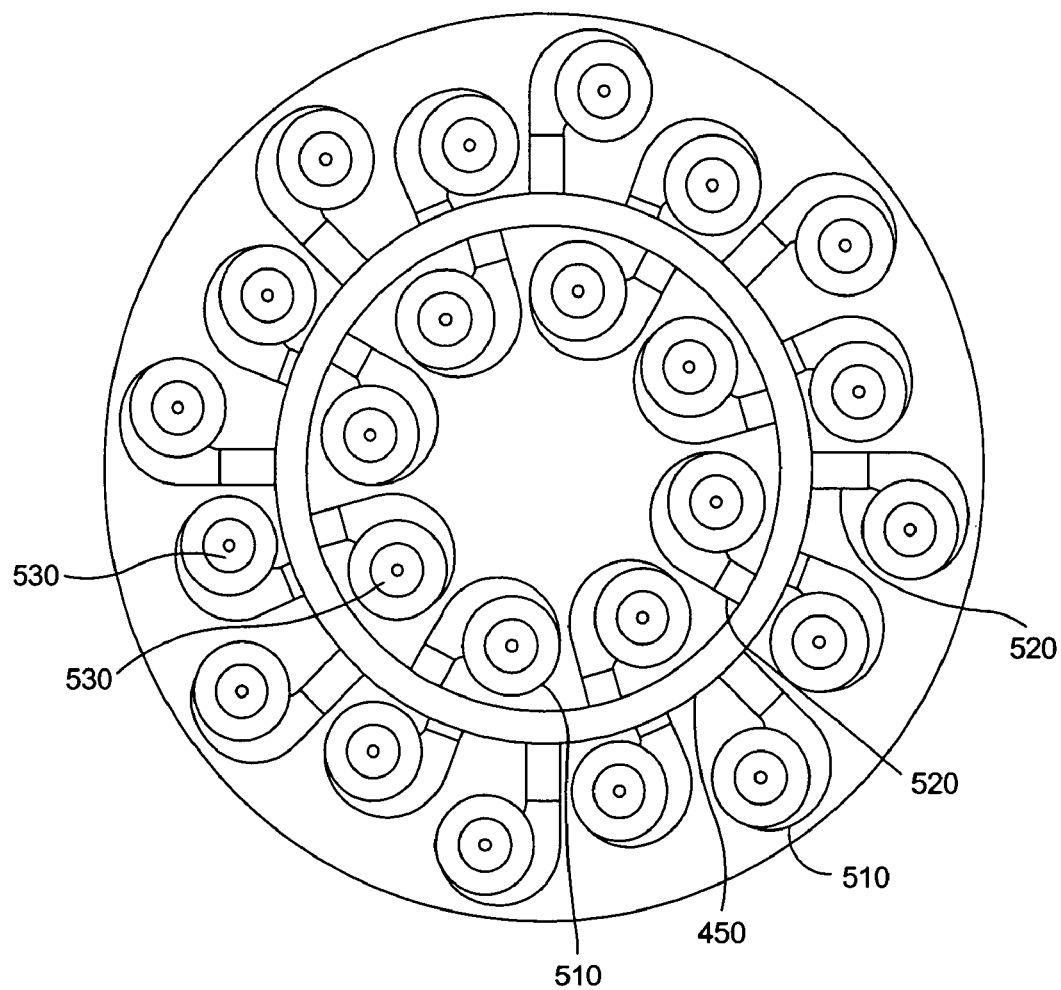
FIG. 5 illustrates another sectional view of the reactor of FIG. 1.

FIG. 5 shows a top down view of the tertiary cyclones 510 along a section line "C-C" as shown in FIG. 1. Tertiary cyclones 510 receive their input from interior plenum 450 via tertiary cyclone inlets 520. Tertiary cyclone outlets 530 direct the lower density output.

III. Flow Conditions

After entering the initial conduit, the feedstock and catalyst flow enter the contacting conduit and pass through the baffled portion of the contacting conduit. Because of the baffles, the baffled portion of the contacting conduit has a reduced hydraulic diameter.

The flow rate of the feedstock introduced into the reactor is selected to provide a desired flow rate in the contacting conduit of the reactor. One benefit of having a baffled contacting conduit is that a plug flow type flow regime can be achieved at lower velocities. Achieving plug flow at lower velocities allows a shorter reactor to provide the same contact time between feedstock and catalyst as compared to a reactor requiring higher flow velocities. One way to characterize whether the feedstock flow has suitable plug flow characteristics is by determining a Peclet number for the proposed flow conditions.

The Peclet number is a dimensionless number that reflects the relative departure from plug flow of gas through the catalyst in a reactor. A Peclet number of infinity (zero dispersn) is ideal plug flow, while a Peclet number less than 4 corresponds to a more completely mixed reactor. For purposes of the present invention, the "Peclet number" ($N_{Pe}$) is defined by the following equation:

$$N_{Pe} = \frac{(U_g)(L)}{D}$$

wherein $U_g$ is the gas superficial velocity through the catalyst; L is the depth of the fluidized bed; and D is the axial gas dispersion coefficient. The axial dispersion coefficient, D, also referred to as the axial gas diffusion coefficient, is in units of area/time, and is preferably determined by tracer experimentation as would be appreciated by one skilled in the art. Note that the smaller the pitch for the baffles in the contacting conduit, the smaller the value of D will likely be.

In an embodiment, in order to achieve a flow condition having a desired axial Peclet number in the baffled portion of the contacting conduit, the feedstock is flowed through the contacting conduit at a superficial gas velocity of at least 5 ft/sec (1.52 m/sec), 6 ft/sec (1.83 m/sec), or at least 8 ft/sec (2.44 m/sec), or at least 10 ft/sec (3.05 m/sec), or at least 12 ft/sec (3.66 m/sec), or at least 15 ft/sec (4.57 m/sec). In another embodiment, the feedstock is flowed through the contacting conduit at a superficial gas velocity of 20 ft/sec (6.1 m/sec) or less, or 15 ft/sec (4.57 m/sec) or less, or 12 ft/sec (3.66 m/sec) or less.

In an embodiment, the axial Peclet number for the feedstock flow in the reactor, both the contacting conduit and the connecting conduit, is at least 8, or at least 10, or at least 12, or at least 15, or at least 17, or at least 20, or at least 25. In yet another embodiment of the invention, the connecting conduit has a Peclet number greater than the Peclet number of the contacting conduit.

The superficial gas velocity used within the reactor also influences the density of catalyst within the reactor. At superficial gas velocities according to the invention, the catalyst in the reactor does not form a conventional dense bed while still providing a feedstock flow with a high degree of plug flow character. At superficial gas velocities according to the invention, the catalyst density within the contacting conduit can be at least 3 lbs/ft$^3$ (48.06 kg/m$^3$), or at least 4 lbs/ft$^3$ (64.07 kg/m$^3$), or at least 5 lbs/ft$^3$ (8.09 kg/m$^3$), or at least 6.5 lbs/ft$^3$ (104.1 kg/m$^3$), or at least 8 lbs/ft$^3$ (128.1 kg/m$^3$), or at least 10 lbs/ft$^3$ (160.2 kg/m$^3$). Alternatively, the catalyst density within the contacting conduit can be 14 lbs/ft$^3$ (224.3 kg/m$^3$) or less, or 12 lbs/ft$^3$ (192.2 kg/m$^3$) or less, or 10 lbs/ft$^3$ (160.2 kg/m$^3$) or less, or 8 lbs/ft$^3$ (128.1 kg/m$^3$) or less.

One advantage of having a catalyst density and superficial gas velocity according to the invention is that the amount of reactor volume and height required to operate a reactor is reduced or minimized relative to a riser reactor. Because of the reduced superficial gas velocity, the catalyst density in a reactor according to the invention is higher, leading to increased conversion rates while maintaining highly plug-flow like conditions and maintaining a high axial Peclet number for the gas flow.

In another embodiment, cooling tubes can be used as the baffles. In such an embodiment, the cooling tubes are also used to reduce the temperature gradient between the top and the bottom of the reaction area in the reactor. In an embodiment, the reaction area comprises the portion of the reactor from the bottom of the fluidized bed of particles to the top of the connecting conduit. The oxygenates-to-olefin conversion reaction is an exothermic reaction. During a conversion reaction, feedstock will initially contact the molecular sieve catalyst in the catalyst bed in the initial conduit. Contact with the catalyst will cause the feedstock to react to form olefin as the feedstock flow moves up through the initial conduit and contacting conduit. The heat generated by the conversion reaction will produce a temperature gradient within the reactor. If no cooling is available, the feedstock flow will increase in temperature as the flow travels up through the reactor. Due to this temperature gradient, feedstock which reacts almost immediately to form an olefin will undergo conversion at a different temperature than feedstock which is converted at a higher point in the reactor. A more uniform conduit temperature is achieved using internal cooling rather than by using higher catalyst re-circulation rate to reduce temperature rise. The lower catalyst re-circulation rate reduces catalyst loading and catalyst losses from the reactor at the same oxygenate conversion level compared to a reactor with no internal cooling and a higher catalyst re-circulation rate.

Figure 6:
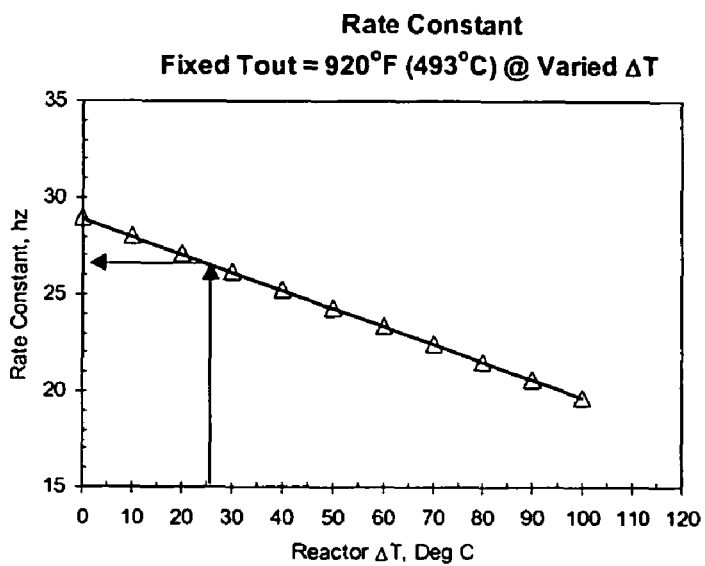
FIG. 6 presents a graph plotting predicted changes in reaction rate for an oxygenates-to-olefin conversion reaction.

FIG. 6 shows that the overall rate constant for the conversion reaction is expected to be reduced by increased temperature gradients in the reactor. A temperature gradient reflects the fact that the feedstock flow will increase in temperature as the flow travels up through the reactor. Thus, feedstock toward the bottom of the reactor will react at a lower temperature than feedstock toward the top of the reactor. If cooling is provided within the reactor, the conversion reaction can occur at a more uniform temperature throughout the reactor. In FIG. 6, an expected conversion rate is shown for reactions with a fixed output temperature of 920° F. (493° C.) and varying temperature gradients within the reactor. The larger the temperature gradient, the lower the temperature is for the conversion reaction at the bottom of the reactor, such as in the fluidized bed. Thus, for a fixed reactor output temperature, a larger temperature gradient corresponds to a lower overall reaction temperature in the reactor. This results in decreasing conversion rates within a reactor as the temperature gradient increases at a fixed output temperature.

Figure 7:
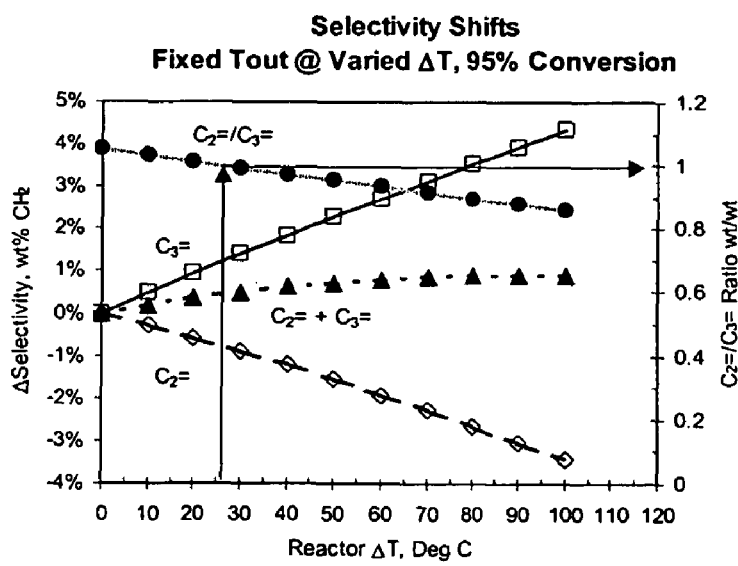
FIG. 7 presents a graph plotting predicted changes in reaction selectivity for an oxygenates-to-olefin conversion reaction.

In addition to reducing the conversion rate, temperature gradients within a reactor also change the products of a conversion reaction. FIG. 7 shows an example of how a temperature gradient in the reactor impacts the conversion of oxygenate feedstock into ethylene and propylene. In FIG. 7, an expected amount of ethylene and propylene production ($C_2$ and $C_3$ olefins) is shown relative to the temperature gradient in the reactor at a fixed reactor outlet temperature of 920° F. (493° C.). If there is no temperature gradient, FIG. 7 shows a predicted ratio of ethylene to propylene of about 1:1, with a slight preference toward production of ethylene. When a temperature gradient exists between the top and bottom of the reactor, the lower temperatures in the lower portion of the reactor lead to increased propylene production at the expense of ethylene. For example, when the temperature gradient in the reactant is 70° C., the weight ratio of ethylene to propylene produced in the conversion reaction is 0.9. Note that the combined percentage of ethylene and propylene produced by the conversion reaction, relative to all products of the conversion reaction, increases slightly as the temperature gradient increases. However, this small increase is more than offset by the lower overall conversion rate when a temperature gradient exists within the reactor.

In an embodiment, the temperature of the feedstock and catalyst flow as it leaves the contacting conduit is 400° C. or greater, or 425° C. or greater, or 450° C. or greater, or 475° C. or greater, or 500° C. or greater, or 525° C. or greater, or 550° C. or greater. In another embodiment, the temperature of the feedstock and catalyst flow as it leaves the contacting conduit is 600° C. or less, or 575° C. or less, or 550° C. or less, or 525° C. or less, or 500° C. or less.

The flow of feedstock and particles then passes into the connecting conduit. Preferably, the connecting conduit has a smaller cross-sectional area than the contacting conduit. In one embodiment, less than 100% of the oxygenate feedstock passing through the contacting conduit is converted into olefins. Similarly, in an embodiment, less than 100% of the oxygenate feedstock passing through the connecting conduit is converted into olefins.

After conversion, the olefins can be separated from the flow and used in another process, such as the formation of polyolefins. After separating out at least one of the converted olefins, the converted olefin can be contacted with another catalyst to form a desired polyolefin.

IV. Additional Reactor Design Parameters and Operating Conditions

An example of a reaction system that benefits from this invention is an oxygenates-to-olefin process. Conventionally, oxygenates-to-olefin processes are carried out in a fluidized bed, fast fluidized bed, or riser reactor configuration where a fluid (gas) flow of a feedstock is passed through a bed of solid catalyst particles. More generally, the processes of this invention are applicable to gas-solids reaction systems where the solids are separated from the gas flow at some point during the reaction process, including systems where the gas is inert. The examples below describe an oxygenates-to-olefin reaction system that can be improved using the separation process of the invention.

Oxygenates used in this invention include one or more organic compound(s) containing at least one oxygen atom. In the most preferred embodiment of the process of the invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols, useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol. Alternately, other non-limiting examples of oxygenates can include, but are not limited to oxygenates containing non-oxygen heteroatoms, such as, sulfur, halides, phosphorus, nitrogen, and the like and combinations thereof.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes, such as methane, ethane, and propane), essentially non-reactive aromatic compounds, and mixtures thereof. The most preferred diluents are water and nitrogen, with water being particularly preferred.

The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In another embodiment, other hydrocarbons are added to a feedstock either directly or indirectly, and include olefin(s), paraffin(s), aromatic(s) or mixtures thereof, preferably propylene, butylene, pentylene, and other hydrocarbons having 4 or more carbon atoms, or mixtures thereof.

In an embodiment of the invention, the solids particles and gas are flowed through the gas-solids reactor at a solids-to-gas mass ratio of about 5:1 to about 50:1. Preferably, the solids particles and gas are flowed through the gas-solids reactor at a solids-to-gas mass ratio of about 8:1 to about 30:1, more preferably from about 10:1 to about 20:1.

In an embodiment, the amount of fresh feedstock fed as a liquid and/or a vapor to the reactor system is in the range of from 0.1 weight percent to about 99.9 weight percent, such as from about 1 weight percent to about 99 weight percent, more typically from about 5 weight percent to about 95 weight percent based on the total weight of the feedstock including any diluent contained therein. The liquid and vapor feedstocks may be the same composition, or may contain varying proportions of the same or different feedstocks with the same or different diluents.

The process of this invention can be conducted over a wide range of temperatures, such as in the range of from about 200° C. to about 1000° C., for example, from about 250° C. to about 800° C., including from about 250° C. to about 750° C., conveniently from about 300° C. to about 650° C., typically from about 350° C. to about 600° C., and particularly from about 350° C. to about 550° C.

Similarly, the process of this invention can be conducted over a wide range of pressures including autogenous pressure. Typically, the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

During the conversion of a hydrocarbon feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example, greater than 75 weight percent, and preferably greater than 78 weight percent. Typically, the amount of ethylene produced in weight percent based on the total weight of hydrocarbon product produced, is greater than 30 weight percent, such as greater than 35 weight percent, for example, greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

The feedstock entering the reactor system is preferably converted, partially or fully, in the first reactor region into a gaseous effluent that enters the disengaging vessel along with the coked catalyst composition. In an embodiment, the disengaging vessel includes cyclone separators configured and/or operated according to the invention. In another embodiment, the disengaging vessel also includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to a regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure, and residence time. In an embodiment, a gas-solids flow exiting a regenerator may be passed through cyclones configured according to the invention.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water, carbon monoxide, and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example, from about 450° C. to about 750° C., and conveniently from about 550° C. to about 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes. The amount of oxygen in the regeneration flue gas (i.e., gas which leaves the regenerator) may be in the range of from about 0.01 mole percent to about 5 mole percent based on the total volume of the gas. The amount of oxygen in the gas used to regenerate the coked catalyst (i.e., fresh or feed gas) is typically at least about 15 mole percent, preferably at least about 20 mole percent, and more preferably from about 20 mole percent to about 30 mole percent, based on total amount of regeneration gas fed to the regenerator.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system.

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the reactor(s). In one embodiment, the regenerated catalyst composition withdrawn from the regeneration system is returned to the reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (pp. 336-337).

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example, from about 0.2 weight percent to about 5 weight percent, and conveniently from about 0.3 weight percent to about 2 weight percent based on the weight of the molecular sieve.

The gaseous reactor effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems, such as ethylbenzene manufacture and other derivative processes such as aldehydes, ketones and ester manufacture, and other associated equipment, for example, various condensers, heat exchangers, refrigeration systems or chill trains, compressors, knock-out drums or pots, pumps, and the like.

Non-limiting examples of these towers, columns, splitters, or trains used alone or in combination include one or more of a demethanizer, preferably a high temperature demethanizer, a deethanizer, a depropanizer, a wash tower often referred to as a caustic wash tower and/or quench tower, absorbers, adsorbers, membranes, ethylene ($C_2$) splitter, propylene ($C_3$) splitter, and butene ($C_4$) splitter.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Typically, in converting one or more oxygenates to olefin(s) having 2 or 3 carbon atoms, a minor amount of hydrocarbons, particularly olefin(s), having 4 or more carbon atoms is also produced. The amount of $C_4$+ hydrocarbons is normally less than 25 weight percent, for example less than 20 weight percent, based on the total weight of the effluent gas withdrawn from the process, excluding water. Typically, therefore, the recovery system may include one or more reaction systems for converting the $C_4$+ impurities to useful products.

V. Description of Solid Particles

In an embodiment, the apparatus and method of the invention are generally useful for separating any solid particles in a gas-solids flow. In another embodiment, the solid particles can be catalyst particles, such as molecular sieve catalyst particles.

Molecular sieve catalyst particles for use in a gas-solids reaction can be synthesized by a variety of methods. In an embodiment, catalyst particles are synthesized by combining a first dried molecular sieve catalyst with water to make a water-catalyst composition, making a slurry from the water-catalyst composition, and drying the slurry to produce a second dried molecular sieve catalyst. The method particularly provides for the re-manufacturing, re-cycling, or re-working of dried or substantially dried, or partially dried molecular sieve catalysts to yield catalyst particles with properties that are acceptable to the user or manufacturer. Such properties are usually observed after the dried molecular sieve catalyst is calcined. These properties include acceptable particle size, particle size distribution, particle density, and particle hardness.

The catalysts of this invention can include any of a variety of molecular sieve components. The components include zeolites or non-zeolites, preferably non-zeolites. In one embodiment, the molecular sieves are small pore non-zeolite molecular sieves having an average pore size of less than about 5 angstroms, preferably an average pore size ranging from about 3 to 5 angstroms, more preferably from about 3.5 to 4.2 angstroms. These pore sizes are typical of molecular sieves having 8 membered rings.

Conventional crystalline aluminosilicate zeolites having catalytic activity are desirable molecular sieves that can be used in making the catalyst of this invention. Examples of such zeolite materials are described in U.S. Pat. Nos. 3,660,274 and 3,944,482. Non-limiting examples of zeolites, which can be employed in the practice of this invention, include both natural and synthetic zeolites. These zeolites include zeolites of the structural types included in the *Atlas of Zeolite Framework Types*, edited by Ch. Baerlocher, W. M. Meier, D. H. Olson, Fifth Revised edition, Elsevier, Amsterdam, 2001.

Zeolites typically have silica-to-alumina ($SiO_2/Al_2O_3$) mole ratios of at least about 2, and have uniform pore diameters from about 3 to about 15 Angstroms. They also generally contain alkali metal cations, such as sodium and/or potassium and/or alkaline earth metal cations, such as magnesium and/or calcium. In order to increase the catalytic activity of the zeolite, it may be desirable to decrease the alkali metal content of the crystalline zeolite to less than about 5 wt. %, preferably less than about 1 wt. %, and more preferably less than about 0.5 wt. %. The alkali metal content reduction, as is known in the art, may be conducted by exchange with one or more cations selected from the Groups IIB through VIII of the Periodic Table of Elements (the Periodic Table of Elements referred to herein is given in *Handbook of Chemistry and Physics*, published by the Chemical Rubber Publishing Company, Cleveland, Ohio, 45th Edition, 1964 or 73rd Edition, 1992), as well as with hydronium ions or basic adducts of hydronium ions, e.g., $NH_4^+$, capable of conversion to a hydrogen cation upon calcination. Desired cations include rare earth cations, calcium, magnesium, hydrogen, and mixtures thereof. Conventional ion exchange methods can be employed.

In another embodiment, the catalyst particles which are flowed through the gas-solids reactor system of this invention are molecular sieve catalysts, such as a conventional molecular sieve. Examples include zeolite as well as non-zeolite molecular sieves, and are of the large, medium, or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW, and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM, and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice*, Second Completely Revised and Expanded Edition, Volume 137, pp. 1-67, Elsevier Science, B.V., Amsterdam, Netherlands (2001).

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$, and $[PO_4]$ tetrahedral units.

Other molecular sieves include those described in EP-0 888 187 B1 [microporous crystalline metallophosphates, $SAPO_4$ (UIO-6)], U.S. Pat. No. 6,004,898 (molecular sieve and an alkaline earth metal), U.S. Pat. No. 6,743,747 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992).

The more preferred silicon, aluminum and/or phosphorous containing molecular sieves, and aluminum, phosphorous, and, optionally, silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn, Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

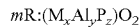

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P, and M as tetrahedral oxides, where M is a metal selected from one of Group IA, IIA, IB, IIIB, IVB, VB, VIIB, VIIB, VIIIB, and Lanthanide's of the Periodic Table of Elements, preferably M is selected from one of the group consisting of Co, Cr, Cu, Fe, Ga, Ge, Mg, Mn, Ni, Sn, Ti, Zn, and Zr. In an embodiment, m is greater than or equal to 0.2, and x, y, and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO molecular sieves useful herein include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and metal containing molecular sieves thereof. Of these, particularly useful molecular sieves are SAPO-18, SAPO-34, SAPO-35, SAPO-44, SAPO-56, and metal containing derivatives thereof. SAPO-34 is particularly preferred.

In another embodiment of the invention, the catalyst used in this invention incorporates aluminophosphate (AlPO) molecular sieves. These molecular sieves can be included as separate crystals or they can be intermixed with other crystalline structures such as by an intergrowth structure. Examples of aluminophosphates include AlPO-5, AlPO-11, AlPO-18, AlPO-31, AlPO-34, AlPO-36, AlPO-37, and AlPO-46.

In one embodiment, the catalyst includes a combination of at least one SAPO and at least one AlPO molecular sieve, wherein the SAPO is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, and SAPO-56, and the AlPO is selected from the group consisting of AlPO-5, AlPO-11, AlPO-18, AlPO-31, AlPO-34, AlPO-36, AlPO-37, and AlPO-46. The sieves can be combined as separate crystals or as intergrown crystals. Preferably, the SAPO is SAPO-18 or SAPO-34, and preferably, the AlPO is AlPO-34 or AlPO-18.

Additional examples of intergrowth molecular sieves useful in this invention include those described in U.S. Patent Application Publication No. 2002-0165089 and International Publication No. WO 98/15496, published Apr. 16, 1998, the descriptions of those sieves incorporated herein by reference. Note that SAPO-18, AlPO-18 and RUW-18 have an AEI framework type, and SAPO-34 has a CHA framework type, and that preferred molecular sieves used herein may comprise at least one intergrowth phase of AEI and CHA framework types, especially where the ratio of CHA framework type to AEI framework type, as determined by the DIFFaX method disclosed in U.S. Patent Application Publication No. 2002-0165089, is greater than 1:1.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

One skilled in the art will also appreciate that the olefins produced by the oxygenates-to-olefin conversion reaction of the present invention can be polymerized to form polyolefins, particularly polyethylene and polypropylene. Processes for forming polyolefins from olefins are known in the art. Catalytic processes are desired. Particularly desired are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691; the catalyst and process descriptions of each being expressly incorporated herein by reference. In general, these methods involve contacting the olefin product with a polyolefin-forming catalyst at a pressure and temperature effective to form the polyolefin product.

VI. Examples

Reaction kinetic rates for methanol conversion were first developed on a laboratory bench-top scale with SAPO catalyst under the conditions of pressure, temperature, and WHSV to be used in the simulations. In order to demonstrate the beneficial effect of a reactor with a contacting conduit operating at an axial Peclet number of at least 8 and the further benefits of operating with a connecting conduit operating at an axial Peclet number greater than the Peclet number of the contacting conduit, a series of computer model reactor simulations were conducted employing the kinetics developed in the laboratory. The computer model was calibrated based on comparison to pilot plant operations. Simulations of ideal continuously stirred tank reactors ("CSTR's") in series were used to approximate plug flow performance and to estimate the Peclet number in each conduit. This methodology is valid since residence time distribution curves (i.e., extent of mixing) of reactors can be expressed in terms of axial Peclet numbers or number of CSTR's in a series. Thus, a series of CSTR's can be used to approximate the residence time distribution corresponding to a certain Peclet number.

The comparative simulations conducted for illustrative purposes of this invention were performed under identical conditions of average temperature, pressure, and conversion. The simulations correspond to performance over a SAPO catalyst with pure methanol feed. Each reactor consisted of a contacting and a connecting conduit, described by axial Peclet numbers. Reactors A, B, and C all show improved performance over reactors having Peclet numbers less than 8. Reactors B and C, when compared to Reactor A, show that performance was improved even more when the Peclet number of the connecting conduit is greater than that of the contacting conduit.

tors A, B, and C, all show a high POS at identical methanol conversion and reactor configurations and process conditions yielding a Peclet number of 8 or more. Reactors B and C show a continued improvement in POS when the Peclet number of the connecting conduit is increased over the Peclet number of the contacting conduit. The combination of the axial Peclet number greater than 8 in the contacting conduit combined with an axial Peclet number in the connecting conduit that is 10% or greater than the axial Peclet number of the contacting conduit lead to an overall higher POS at the reactor effluent.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

What is claimed is:

1. A method for converting oxygenates to olefins, comprising:
   a) contacting a molecular sieve catalyst with an oxygenate feedstock in an initial conduit;
   b) flowing the molecular sieve catalyst through a contacting conduit having an axial Peclet number for a gas portion of the flow of 8 or more and containing a plurality of baffles, and having a diameter larger than the initial conduit, at a superficial velocity of 5 feet per second (1.52 msec) or greater; and
   c) passing the molecular sieve catalyst and oxygenate feedstock into a connecting conduit having a diameter smaller than that of the contacting conduit, wherein the connecting conduit has a Peclet number greater than the Peclet number of the contacting conduit.

2. The method of claim 1, wherein the contacting conduit has a hydraulic diameter of 72 inches (1.83 m) or less.

3. The method of claim 1, wherein the connecting conduit has a Peclet number at least 10% greater than the Peclet number of the contacting conduit.

4. The method of claim 1, wherein the connecting conduit further comprises at least one baffle to further reduce backmixing.

5. The method of claim 1, wherein a temperature gradient extending from an entrance of the contacting conduit to an exit of the contacting conduit is maintained at 100° C. or less.

6. The method of claim 5, wherein the temperature gradient is maintained at 50° C. or less.

TABLE 1

Reactor Performance vs. Peclet Number

| | Reactor | | | | | | | | |
|---|---|---|---|---|---|---|---|---|---|
| | A | | | B | | | C | | |
| Reactor Charateristic | NPe | # CSTR's | Conv. (wt. %) | NPe | # CSTR's | Conv. (wt. %) | NPe | # CSTR's | Conv. (wt. %) |
| Contacting Conduit | 8 | 2.67 | 50% | 8 | 2.67 | 50% | 8 | 2.67 | 50% |
| Connecting Conduit | 8 | 2.67 | 98% | 9 | 3.11 | 98% | 16 | 6.4 | 98% |
| POS at Connecting Conduit Exit (wt. %) | | 75.8 | | | 75.9 | | | 76.3 | |

As stated earlier, a higher production rate of ethylene and propylene relative to the total of ethylene and propylene and all other reactor product constituents on a weight percent basis, or prime olefin selectivity ("POS"), is preferred. Reac- 7. The method of claim 6, wherein the temperature gradient is maintained at 20° C. or less.

8. The method of claim 1, wherein the molecular sieve catalyst is a silicoaluminophosphate molecular sieve.

9. The method of claim 5, wherein one or more of the baffles in the contacting conduit comprises one or more cooling tubes.

10. The method of claim 9, wherein the temperature gradient is maintained by flowing steam or boiling water through the one or more cooling tubes.

11. The method of claim 5, wherein the temperature gradient is maintained by flowing boiling water through a first plurality of cooling tubes and flowing steam through a second plurality of cooling tubes.

12. The method of claim 1, wherein the catalyst and feedstock flow leave the contacting conduit at a temperature of 400° C. or greater.

13. The method of claim 1, wherein at least a portion of the contacting conduit has a hydraulic diameter of from 10 inches (0.25 m) to 24 inches (0.61 m).

14. The method of claim 1, wherein the catalyst and feedstock flowing through the contacting conduit flow at a catalyst density of from 4 lb/ft$^3$ (64.07 kg/m$^3$) to 20 lb/ft$^3$ (320.4 kg/m$^3$).

15. The method of claim 14, wherein the catalyst and feedstock flowing through the contacting conduit flow at a catalyst density of from 8 lb/ft$^3$ (128.1 kg/m$^3$) to 12 lb/ft$^3$ (192.2 kg/m$^3$).

16. The method of claim 1, wherein the catalyst and feedstock flowing through the contacting conduit flow at a superficial gas velocity of from 6 ft/sec (1.83 m/sec) to 20 ft/sec (6.1 m/sec).

17. The method of claim 16, wherein the catalyst and feedstock flowing through the contacting conduit flow at a superficial gas velocity of from 8 ft/sec (2.44 m/sec) to 15 ft/sec (4.57 m/sec).

18. The method of claim 5, wherein the temperature gradient is maintained by:
 selecting a temperature for the exit of the contacting conduit; and
 controlling a temperature at the entrance of the contacting conduit to achieve a ratio of $C_2$ olefins versus $C_3$ olefins of from about 0.8 to 1 to about 1.2 to 1.

19. The method of claim 1, wherein the initial conduit has a diameter less than the contacting conduit.

* * * * *